United States Patent [19]

Carroll et al.

[11] Patent Number: 5,298,499
[45] Date of Patent: Mar. 29, 1994

[54] S-2-(SUBSTITUTED ETHYLAMINO)ETHYL PHOSPHOROTHIOATES

[75] Inventors: Frank I. Carroll, Durham; Philip Abraham, Cary, both of N.C.

[73] Assignee: Research Triangle Institute, Research Triangle Park, N.C.

[21] Appl. No.: 726,286

[22] Filed: Jul. 5, 1991

[51] Int. Cl.⁵ .................... A61K 31/66; C07C 229/00; C07C 69/66; C07D 285/01
[52] U.S. Cl. ..................................... 514/114; 514/119; 558/169; 558/170; 558/172; 558/176; 548/187; 548/186; 548/111; 544/5
[58] Field of Search ................ 558/169, 170, 172, 176; 514/119, 114

[56] References Cited

U.S. PATENT DOCUMENTS

| | | | |
|---|---|---|---|
| 3,501,557 | 3/1970 | Brois | 558/105 |
| 3,501,557 | 3/1970 | Brois | 558/105 |
| 3,517,087 | 6/1970 | Coleman | 558/105 |
| 3,892,824 | 7/1975 | Piper et al. | 558/166 |
| 4,424,216 | 1/1984 | Cerami et al. | 514/114 |
| 4,567,169 | 1/1986 | Lavielle et al. | 547/881 |

OTHER PUBLICATIONS

Carroll et al; Journal of Medicinal Chemistry (1990) 33(9) 2501–2508.
Chemical Abstracts 87(19)1464826 (1977).
Chemical Abstracts 87(17) 133800d (1977).

*Primary Examiner*—John M. Ford
*Assistant Examiner*—Matthew V. Grumbling
*Attorney, Agent, or Firm*—Oblon, Spivak, McClelland, Maier & Neustadt

[57] ABSTRACT

Substituted phosphorothioate derivatives and pharmaceutical compositions thereof as potential antiradiation agents are disclosed.

11 Claims, No Drawings

S-2-(SUBSTITUTED ETHYLAMINO)ETHYL PHOSPHOROTHIOATES

BACKGROUND OF THE INVENTION

1. Field of the Invention

The present invention relates to novel phosphorothioate compounds and pharmaceutical preparations thereof which are useful in reducing the effects of ionizing radiation on animal cells.

2. Discussion of the Background

The events leading up to the end of World War II were punctuated by the dropping of two nuclear bombs on the cities of Hiroshima and Nagasaki. The death, suffering, and permanent damage inflicted on the residents revealed just how devastating the effects of ionizing radiation could be.

These events initiated a vigorous research program into radioprotective agents to minimize the effects of radiation. The most effective agent to emerge from these efforts was S-2-[3-aminopropylamino]ethylphosphorothioic acid (1, WR2721) (U.S. Pat. No. 3,892,824).

    1

Compound 1, is believed to undergo in vitro hydrolysis by the action of phosphatase enzymes to yield compound 2

    2 which is also known to be a radioprotective agent (T. R. Sweeney "A Survey of Compounds From the Antiradiation Drug Development Program of the U.S. Army Research and Development Command", Walter Reed Army Institute of Research, 1979).

Additional research has discovered that 2-(2α-carbamidoethylamino)ethanethiol 3 also shows good radioprotective activity, comparable to that of compound 2 (F. I. Carroll and M. E. Wall, *J. Pharm. Sci.*, 1970, 59, 1350).

    3

The phosphorothioate derivative of compound 3 has been prepared (4 WR6458) (U.S. Pat. No. 3,501,557) however the

    4 result was a more toxic compound and therefore could not be tested at dose levels comparable to compound 1. At doses lower than the toxic level, no radioprotective activity was observed (see T. R. Sweeney ibid.). It has also been reported that compound 4 is effective for reducing mucin viscosity when administered in dosage rates ranging from 1-100 mg/kg/day (U.S. Pat. No. 4,424,216).

While anti-radiation drug treatment began as an effort to improve the survivability of nuclear war, a more practical aspect of the these research programs is the development of treatments for protecting cancer radiation therapy recipients. Clinical radiotherapy of malignant tumors unavoidably subjects adjacent healthy tissue to damaging radiation. It is desirable to chemically protect normal tissue from radiation injury without adversely affecting the radiosensitivity of the tumor. Even though both malignant and healthy tissue show comparable uptake of the radioprotective agent WR2721, the deficient vascular network of solid tumors reduces the uptake of the radioprotective agent. This partitioning allows for greater effectiveness in radiation treatment. The partitioning effect can be magnified by increasing the uptake of agents in healthy tissue or decreasing the uptake in tumor cells.

There remains a search for radioprotective agents with improved bioavailability and an increased partition coefficient.

SUMMARY OF THE INVENTION

Accordingly, one object of the present invention is to provide a novel phosphorothioate compound which, upon administration exhibits high radioprotective activity.

Another aspect of the present invention provides pharmaceutical compositions of phosphorothioate compounds.

Another aspect of the present invention provides a method of providing radiation protection.

This and other objects are achieved by the practice of providing compounds of the formula 5

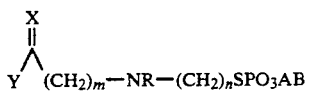    5 where

X equals O, S, N—R';

Y equals N(R")R''', S—R";

R equals H, $C_{1-20}$ alkyl, benzyl, phenyl;

R', R", and R''', is each independently H, $C_{1-6}$ alkyl, halosubstituted $C_{1-6}$ alkyl, $C_{3-6}$ cycloalkyl, $C_{3-6}$ cycloalkyl substituted $C_{1-6}$ alkyl, $H_2NC(O)$ or $SO_2R''''$;

wherein R'''' is phenyl, p-anisyl, p-chlorophenyl, tolyl, $C_{1-6}$ alkyl or amino;

wherein R" and R' are able to combine to form a ring of 5-7 members, wherein one of the members of the ring of 5-7 members may be $O_2$;

m and n are each independently an integer from 1-4;

A and B are each independently H, $C_{1-6}$ alkyl or alkali metal;

or hydrates thereof.

The present invention can also be practiced by providing compounds of the formula 6:

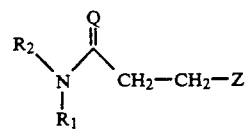    6 when

Z equals NH—CH$_2$—CH$_2$—S—S—CH$_2$—CH$_2$—NHCH$_2$CH$_2$C(NH)NH$_2$,

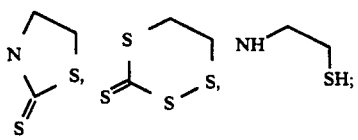

Q equals $H_2$, O; and
$R_1$ and $R_2$ are each independently H, $CH_3$, s-butyl and t-bu$O_2$C;
or hydrates thereof.

DETAILED DESCRIPTION OF THE PREFERRED EMBODIMENTS

The present invention relates to compounds and compositions for reducing the harmful effects of ionizing radiation. Soon after the beginning of the atomic era, it was recognized that deleterious effects result from prolonged exposure to X-ray radiation. Current estimates are that a dose of 6 GY over a period of 6–7 days would kill 90% of the exposed population. A dose of 4.5 GY would kill 50% and 3 GY would kill 10%. It is believed the survivors of the Japanese bomb attacks received on average ~ 0.25 GY radiation.

The sequence of events leading from the initial absorption of radiation energy to the ultimate death of the organism is complex and incompletely understood. At its simplest level, ionizing radiation results in the generation of free radicals which result in molecular alterations in living organisms. For a more detailed explanation see Kirk-Othmer vol. 19, pp. 801–807.

The present invention provides for compounds of the formula 5:

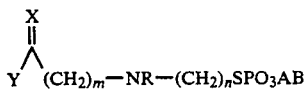

where
X equals O, S, N—R';
Y equals N(R")R''', S—R";
R equals H, $C_{1-20}$ alkyl, benzyl, phenyl;
R', R", and R''', is each independently H, $C_{1-6}$ alkyl, halosubstituted $C_{1-6}$ alkyl, $C_{3-6}$ cycloalkyl, $C_{3-6}$ cycloalkyl substituted $C_{1-6}$ alkyl, $H_2NC(O)$ or $SO_2R''''$;
wherein R'''' is phenyl, p-anisyl, p-chlorophenyl, tolyl, $C_{1-6}$ alkyl, $H_2NC(O)$ or amino;
wherein R" and R' are able to combine to form a ring of 5–7 members, wherein one of the members of the ring of 5–7 members may be $SO_2$;
m and n are each independently an integer from 1–4;
A and B are each independently H, $C_{1-6}$ alkyl or alkali metal;
or hydrates thereof.

In a preferred embodiment both m and n are 2.

In accordance with the present invention, compounds where X is S and Y is N(RII)RIII to form a substituted thioamide are particularly effective in providing radioprotection. In addition, compounds where X is NR' and Y is N(R")R''' to form an amidine or cyclic amidine group are also very effective.

The present invention also provides for compounds of the formula 6:

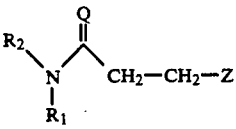

when
Z equals NH—$CH_2$—$CH_2$—S—S—$CH_2$—$CH_2$—NH$CH_2CH_2$C(NH)$NH_2$,

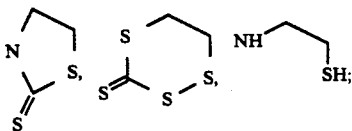

Q equals $H_2$, O; and
$R_1$ and $R_2$ are each independently H, $CH_3$, s-butyl and t-bu$O_2$C;
or hydrates thereof.

The compounds of the present invention include S-2-[2'-N-Methylcarbamidoethylamino]ethyl Lithium Hydrogen Phosphorothioate, S-2-(2'-Carbamidoethylamino)ethyl Lithium Hydrogen Phosphorothioate, S-2-[2'-(tert-Butylcarbamido) ethylamino]ethyl Dilithium Phosphorothioate, S-2-(2'-N-Methylthiocarbamidoethylamino)ethyl Lithium Hydrogen Phosphorothioate, S-2-[Thiocarbamidoethylamino]ethyl Lithium Hydrogen Phosphorothioate, S-2-[2'-(N-Methylamidino)ethylamino] ethylphosphorothioic Acid, S-2-(2'-Amidinoethylamino) ethylphosphorothioic Acid, and S-2-[2'-(4,5-Dihydroimidazoyl) ethylamino]ethyl Lithium Hydrogen Phosphorthioate.

The compounds of the present invention also include: S-2-(thiocarboxamidoethylamino)ethyl lithium hydrogen phosphorothioate, S-2-(2'-Amidinoethylamino)ethyl phosphorothioic acid, S-2-[2'-(N-Methylamidino)ethylamino] ethylphosphorothioic acid, S-2(2'-N-(p-Methoxybenzenesulfonyl)amidinoethylamino]ethyl lithium hydrogen phosphorothioate, S-2[2'-N-(p-Chlorobenzenesulfonyl)amidinoethylamino]ethyl lithium hydrogen phosphorothioate, S-2[2'-N-(p-Methylbenzenesulfonyl) amidinoethylamino]ethyl lithium hydrogen phosphorothioate, S-2-[2'-(N-Ethylcarboxamido)ethylamino]ethyl dilithium phosphorothioate, S-2[N-(Methylsulfonyl)amidinoethyl amino]ethyl lithium hydrogen phosphorothioate, S-2[N-(Isopropylsulfonyl)amidinoethylamino]ethyl dilithium phosphorothioate, S-2-[2'-(N-Cyclopropylmeythyl]carboxamido) amino]ethyl dilithium phosphorothioate, S-2-[N-(Aminosulfonyl)amidinoethylamino]ethyl dilithium phosphorothioate, S-2-[2'-Trifluoroethylcarboxamidoethylamino]ethyl dilithium phosphorothioate, S-2-[2'-(tert-Butylcarboxamido)ethylamino]ethyl dilithium phosphorothioate, S-2-[2'-(1-Methylpropylcarboxamido)ethylamino]ethyl dilithium phosphorothioate, S-2-[2'-(N-Carbamyl)carbamidoethylamino] ethylphosphoro-thioic acid, S-2-(3'-Amidinopropylamino)ethylphosphorothioic acid, S-2-[2'-(Δ²-1,2,4-thiadiazolyl 1,1-dioxide)ethylamino]ethyl lithium hydrogen phosphorothioate, S-2-[2'-(tert-Butylthiocarboxamido)ethylaminolethyl lithium hydrogen phosphorothioate, [N-(1-Methylpropyl)carboxamidoethyl]-2-thioxo-3-thiazolidine, 4-(3-tert-Butyloxycarbamidopropyl)-5,6-dihydro-1,2,4-3(4H)-dithiazinethione, 4-(3-Aminopropyl)-5,6-dihydro-1,2,4-3(4H)- dithiazinethione, 4-(21-N-Carbamidoethyl)5,6-dihydro-1,2,4-3(H)-dithiazinethione, N-[2'-Amidinoethyl]aminoethanethiol dihydrochloride, S-2-(2'-Cyclopropylmethylamidinoethylamino)ethyl phosphorothioic acid, Bis-[N,N-(2'-Amidinoethyl)aminoethyl]disulfide tetrahydrochloride, 4-[3-tert-Butyloxy-(N-methyl)carbamidopropyl]-5,6-dihydro-1,2,4-3(4H)-dithiazinethione, and 4-(3-Methylaminopropyl)-5,6-dihydro-1,2,4-3(4H)-dithiazinethione Hydrochloride.

In addition to the novel compounds described above, the present invention relates to pharmaceutical compositions of compounds of formula 5. The pharmaceutical compositions may be prepared by using formulating excipients, such as solid, liquid and semi-liquid carriers, such as methyl cellulose, starch, various sugars, e.g., lactose, sucrose, sugar alcohols, such as sorbitol, and mannitol may be used. As liquid carriers water, lower alcohols may be used alone or in combination with each other or with the carriers mentioned above. The compositions may further contain stabilizers, fungicidal agents, bacteriostatic agents, antimicrobial agents, antioxidants, aromas, ph-adjusters, osmotic pressure controlling components, such as various buffers and sodium chloride. compositions are prepared such that a dose rate of 150-600 mg/kg can be conveniently administered.

The compositions of the present invention may be administered orally, intraperitoneally, or intramuscularly. Compositions may be provided as tablets, capsules, or injectable liquids. Compositions provided as injectable liquids are preferred and intraperitoneal injection is the most effective means of administration.

Optimal radioprotection is achieved after 30 minutes for intraperitoneal injection and 60 minutes for oral ingestion.

Dosage range provided for by the present invention are 100–1,000 mg/kg, more preferably 300–600 mg/kg.

The phosphorothioate derivatives of the present invention are useful for reducing the effects of ionizing radiation. These compounds are believed to react with free radicals to form a more stable thio radical. These compounds are further useful against the side effects of cancer chemotherapy and radiation treatments.

The replacement of the terminal -NH$_2$ of WR2721 with a thioamide or amidine group results in a more strongly basic group. This modification provides a compound with greater lipid solubility and therefore better bioavailability. Improved lipid solubility enhances the partitioning of the agent between vascular tissue and solid tumors as solid tumors possess a lower lipid content. This translates to more effective radioprotection at smaller dosages than previously obtainable.

Other features of the invention will become apparent in the course of the following descriptions of exemplary embodiments which are given for illustration of the invention and are not intended to be limiting thereof.

EXAMPLE 1

Synthesis of S-2-[2'-N-Methylcarbamidoethyl-amino]ethyl Lithium Hydrogen Phosphorothioate (11)

β-chloroethomycarbonyl-β-alanine (7)

Chloroethyl chloroformate (7.15 g 0.5 mol) and a solution of NAOH (20 g, 0.5 mol) in 100 mL of H$_2$O were added simultaneously over a period of 1 h to a stirred solution of β-alanine (44.5 g, 0.5 mol) and NAOH (20 -g, 0.5 mol) in 500 mL of H$_2$O. The pH of the reaction mixture was maintained between 7-8 during the addition. After stirring for 4 h at room temperature, the reaction mixture was extracted with ether. The aqueous mixture was extracted with ethyl acetate after acidification of the aqueous layer to pH 2-3 with 6 N HCl. The ethyl acetate solution was washed with NaCl solution and dried over Na$_2$SO$_4$. The residue after removal of the solvent was recrystallized from ethyl acetate-hexane to give 92.9 g (93%) of 7: mp 69°–70° C.; $^1$H NMR (CDCl$_3$) δ 2.46 (t, 2, —CH$_2$CO$_2$), 3.47 (m, 2, NCH$_2$), 3.67 (t, 2, CH$_2$Cl), and 4.34 (t, 2, OCH$_2$) Anal. (C$_7$H$_{10}$ClNO$_4$): C, 36.94; H, 5.17: Cl, 18.18; N, 7.16.

N-Methyl-β-chloroethoxycarbamyl-β-alanine Amide (8) A solution of 7 (50 g, 0.26 mol) in 350 mL of CHCl$_3$ was heated to reflux with SOCl$_2$ (61 mL) for 1 h. The solvents were removed under reduced pressure and the residue was dissolved in 50 mL of toluene and again evaporated to dryness under reduced pressure to provide the acid chloride of 7. A solution of methylamine (15.9 g, 0.52 mol) in 200 mL of CHCl$_3$ was added dropwise to a solution of the acid chloride in 350 mL of CHCl$_3$ at dry ice-acetone temperature over a period of 1.5 h. When the addition was complete, the mixture was allowed to come to room temperature and was stirred overnight. The precipitated methylamine hydrochloride was removed by filtration and washed with CHCl$_3$. The combined CHCl$_3$ solution was washed with saturated NaCl solution and evaporated to dryness. The resulting solid was recrystallized from CHCl$_3$-hexane to give 35.2 g (66%) of 8: mp 125°–126° C.; $^1$H NMR (CDCl$_3$) δ 2.42 (t, 2, CH$_2$CO), 2.81 (d, 3, NCH$_3$), 3.46 (m, 2, NCH$_2$), 3.66 (t, 2, CH$_2$Cl) and 4.29 (t, 2, OCH$_2$)- Anal. (C$_7$H$_{13}$ClN$_2$O$_3$): C, 40.23; H, 6.29; Cl, 16.92; N, 13.41.

N-[2-(N'-Methylcarbamido)ethyl]oxazolidinone (9). To a suspension of hexane washed NaH [(50% suspension), 6.8 g, 0.16 mol] in 200 mL of dry DMF was added a solution of 8 (33.28 g, 0.16 mol) in 100 ML of DMF over a period of 1 h. The precipitated NaCl obtained after stirring overnight was separated by filtration, and the solution was evaporated to an oil under reduced pressure. The product was purified by silica gel column chromatography using 20% MeOH-CH$_2$Cl$_2$ as the eluant to give 16.5 g (94%) of 9; $^1$H NMR (CD$_3$OD) δ 2.44 (t, 2, CH$_2$CO), 2.71 (s, 3, NCH$_3$), 3.51 (t, 2, NHCH$_2$), 3.62 (t, 2, NCH$_2$ oxazolone) and 4.31 (t, 2, CH$_2$O)- Anal. (C$_7$H$_{12}$N$_2$O$_3$.0.25 H$_2$O): C, 47.28; H, 6.96; N, 15.59.

A 25.4 g (0.12 mol) run gave 16.2 g (77%) of 9b.

2'-[N-Methylcarbamidoethylamino]ethyl Bromide Hydrobromide (10). A solution of the oxazolidinone 9 in excess acetic acid saturated with HBr was stirred at room temperature overnight. The excess HBr and some acetic acid was removed under reduced pressure. Dilution of the remaining solution with 10 mL of MeOH followed by careful addition of 100 mL of ether gave the desired product 10. The final purification was achieved by recrystallization from MeOH-ether to yield 32% of 10b: mp 124°–126° C.; $^1$H NMR (CD$_3$OD) δ 2.67 (t, 2, CH$_2$CO), 2.75 (s, 3, NCH$_3$), 3.31 (t, 2, CH$_2$-N), 3.53 (t, 2, NCH$_2$) and 3.72 (t, 2, CH$_2$Br). Anal. (C$_6$H$_{14}$Br$_2$N$_2$O): C, 24.83; H, 4,89; Br, 55.00; N, 9.63.

S-2-[2'-N-Methylcarbamidoethylamino]ethyl Lithium Hydrogen Phosphorothioate (11). To a stirred solution of trilithium thiophosphate (0.696 g, 3 mmol) in 3 mL of H$_2$O was added bromo compound 10 as a solid. After all the solid dissolved, 1.5 mL of DMF was added, and stirring was continued for 3.5 h. At this point a $^{31}$P NMR spectrum indicated that all the trilithium thiophosphate had reacted. A small amount of solid was removed by centrifugation. The clear supernatant was diluted with 30 mL of DMF while maintained in a water bath at 20° C. The mixture was stirred for 30 min and again centrifuged. The supernatant was separated by decantation. The solid was stirred with DMF:ether (1:1) and centrifuged. The residue obtained was stirred with 200 mL ether and separated by filtration. This solid was dried under a stream of $N_2$ to give 0.47 g (63%) of 11: $^1$H NMR ($D_2O$) δ 2.67 (t, 2, $CH_2CH_2CO$), 2.75 (s, 3, $NCH_3$), 2.96 (m, 2, $CH_2CH_2S$), 3.24 and 3.27 (d t, 4, $CH_2NCH_2$); $^{31}$P NMR ($D_2O$) 16.11 ppm (t, J=13 Hz).

Anal. ($C_6H_{14}LiN_2O_4PS.1/3\ H_2O$): C, 27.65; H, 5.80; N, 10.68; P, 11.95; S, 12.16.

This experiment was repeated at 0.1 mol scale three times giving yields of 60, 80 and 88%

EXAMPLE 2

S-2-(2'Carbamidoethylamino)ethyl Lithium Hydrogen Phosphorothioate (12)

This compound was prepared according to the method of Example 1 except ammonia was used in the condensation reaction. 12 was obtained as a white solid: $^1$H NMR ($D_2O$) δ 2.77 (t, 2, $CH_2CH_2CO$—), 3.5 (m, 2, —S—$CH_2CH_2$) and 3.4 (m, 4, —$CH_2$—$N^+H_2CH_2$). $^{31}$P NMR ($H_2O$) 15.63 ppm (t, J=13 Hz). Anal. ($C_5H_{12}LiN_2O_4PS$): C, H, 25.31; 5.25; N, 11.82; P, 13.60; S, 13.57.

A 0.024 mol run gave an essentially quantitative yield of 12.

EXAMPLE 3

S-2-[2'-(tert-Butylcarbamido)ethylamino]ethyl Dilithium Phosphorothioate (13)

This compound was prepared according to the method of Example 1 except t-butylamine was used in the condensation reaction mp >295° C. (dec); $^1$H NMR ($D_2O$) δ 1.32 [s, 9, $C(CH_3)$], 2.38 (t, 2, $CH_2CO$), 2.83 (m, 6, $CH_2NHCH_2CH_2$ S). $^{31}$P NMR ($D_2O$) 16.42 ppm (t, J=10 Hz). Anal. ($C_9H_{19}N_2Li_2O_4PS.0.5\ H_2O$). C, 35.54; H, 6.56; N, 9.18; S, 10.58; P, 10.43; Li, 4.44.

EXAMPLE 4

Preparation of S-2-[Thiocarbamidoethylamino]ethyl Lithium Hydrogen Phosphorothioate (16)

N-(2-Thiocarbamidoethyl)oxazolidinone (14). A mixture of 25 g (0.17 mol) of N-(2-carbamidoethyl)oxazolidinone (prepared according to the preparation of 9 except ammonia was used in the condensation reaction) and 36.8 g (0.09 mol) of Lawesson's reagent was stirred with 790 mL of freshly distilled THF for 2 h at which time the mixture became clear. This mixture on partial concentration under reduced pressure followed by dilution with hexane and cooling gave a precipitate which was collected by filtration and washed with cold ether. Recrystallization from MeOH-ether gave 14.5 g (54%) of 14: mp 141°-142° C.; $^1$H NMR (DMSO-$d_6$) δ 2.69 (t, 2, $CH_2CH_2CS$), 3.52 (m, 4, $CH_2NHCH_2$) and 4.2 (t, 2, $CH_2\overline{CH_2}O$—)—Anal. ($C_6H_{10}\overline{N}_2O_2S$): C, 41.33; H, 5.82; N, 16.03; S, 18.46.

2-(Thiocarbamidoethylamino)ethyl Bromide Hydrogen Bromide (15). Compound 15 was prepared from compound 14 according to the procedure for preparing 10. Recrystallization from MeOH-ether gave 64% of 15: mp 116°-118° C.; $^1$H NMR (DMSO-$d_6$) δ 2.92 (t, 2, $CH_2CH_2CS$), 3.3 (t, 2, $NCH_2CH_2CS$—), 3.48 (t, 2, $CH_2CH_2N$) and 3.71 (t, 2, $CH_2CH_2Br$). Anal. ($C_5H_{12}Br_2N_2S$): C, 20.48; H, 4.15; Br, 54.82; N, 9.56; S, 10.95.

S-2-[Thiocarbamidoethylamino]ethyl Lithium Hydrogen Phosphorothioate (16). To a stirred solution of 5.46 g (0.026 mol) of $Li_3SPO_3.4.2H_2O$ in 130 mL of water was added 8.58 g (0.0294 mol) of 15. Dimethylformamide (65 mL) was added to the solution, and the mixture was stirred for 2.75 h, diluted with 280 mL of $CH_3CN$ and placed in the refrigerator (4° C.) for 6 days. The pale yellow crystals were separated by filtration, washed with $CH_3CN$ (420 mL), ether (420 mL) and dried under vacuum for 6 h to give 5.1 g (65%) of 16: mp 73°-83° C.; $^1$H NMR ($D_2O$) δ 2.94—3.09 [m, 4, —$CH_2CH_2C(S)$], 3.39-3.53 (m, 4, —S—$CH_2$—$CH_2$—NH—) $^{31}$P NMR ($D_2O$) δ 15.63 (J=13 Hz). Anal. ($C_5H_{12}LiN_2O_3PS_2.3\ H_2O$) : C, 19.79; H, 6.09; N, 9.15; P, 10.07; S, 21.15.

EXAMPLE 5

S-2-[2'-N-Methylthiocarbamidoethylamino]ethyl Lithium Hydrogen Phosphorothioate (17)

This compound was prepared according to the method of Example 4, except Compound 9 was treated with Lawesson's reagent. Compound 17 was a white solid. $^1$H NMR ($D_2O$) δ 2.86 (t, 2, $CH_2CH_2CS$), 3.02 (t, 2, $CH_2CH_2$—S), 3.39 (t, 2, $NCH_2CH_2CS$), 3.49 (t, 2, $CH_2CH_2\overline{-S}$) ; $^{31}$P NMR ($D_2O$) 15.57 ppm (t, J=13 Hz). Anal. ($C_6H_{14}LiN_2O_3PS_2.1.5\ H_2O$) C, 25.00; H, 6.01; N, 9.71; P, 10.09; S, 22.29.

EXAMPLE 6

Synthesis of S-2-[2'-(N-Methylamidino)ethylamino] ethylphosiphorothioic Acid (21)

N-(2-Cyanoethyl)oxazolidinone (18). Compound 18 was prepared by modification of a reported procedure by Lynn (U.S. Pat. No. 2,975,187). To a vigorously stirred mixture of 2-oxazolidinone (87 g, 1 mol), 50% sodium hydroxide (w/w, 4 g) and toluene (250 mL) maintained at 55°-60° C., acrylonitrile (106 g, 2 mol) was added dropwise over a period of 30 min. The mixture was then stirred at 80° C. for 1 h and refluxed for 3 h. Additional acrylonitrile (50 mL) was added towards the end of the reaction to drive it to completion. Excess acrylonitrile was removed by distillation, and the residue was left at room temperature overnight. The mixture was filtered, cooled in an ice bath and acidified with concentrated $H_2SO_4$ to ~ pH 1. The salt was removed by filtration, and the filtrate was dried over anhydrous $MgSO_4$. The residue obtained after removal of the solvent under vacuum was dried under high vacuum overnight to give 117 g (84%) of 18 as a colorless oil: $^1$H NMR ($CDCl_3$) δ 2.68 (t, 2, $CH_2CH_2CN$), 3.57 (t, 2, $NCH_2CH_2$), 3.75 (t, 2, $NCH_2\overline{CH_2}O$) and 4.39 (t, 2, $CH_2\overline{H_2}O$—).

The product obtained was sufficiently pure to be used in the next step.

N-[2-(N-methylamidino)ethyl]oxazolidinone Hydrochloride (19). A stirred solution of 18 (10 g, 0.07 mol) in dry $CH_2Cl_2$ (20 mL) and dry methanol (4.6 mL, 0.114 mol) was saturated with dry HCl at −10° C. to −5° C. After saturation, the mixture was stirred at −5° C. to 2° C. for 6 h and concentrated to dryness to give imino ester hydrochloride as a white solid. This compound was dissolved in dry methanol (90 mL) and cooled in a dry ice bath. To the stirred mixture at −40° C. (partial precipitation occurred), methylamine (5.6 g, 0.18 mol)

was added in one portion. Dry methanol (10 mL) was added to facilitate stirring, and stirring was continued for 30 min at −30° C. to −10° C. The mixture was evaporated, and the resulting white solid was recrystallized from methanol-ether to give 10.7 g (72%) of 19 as colorless needles: mp 169°–172° C.; $^1$H NMR (DMSO-$d_6$) δ 2.6 [t, 2, —CH$_2$—C(NH)—], 2.78 (s, 3, —NHCH$_3$), 3.52 [t, 2, —CH$_2$—CH$_2$—C(NH)—], 3.65 (t, 2, —O—CH$_2$—CH$_2$), 4.26 (t, 2, —O—CH$_2$), 8.7 (br s, NH,), 9.5 (br s, NH), 10.1 (br s, NH). Anal. (C$_7$H$_{14}$ClN$_3$O$_2$): C, 40.38; H, 6.82; Cl, 12.13, N, 11.34.

2-(N-Methylamidinoethylamino)ethyl Bromide Dihydrobromide 20. Compound 19 (10 g, 0.048 mol) was added in portions to a well stirred saturated solution of 100 mL of HBr in AcOH at room temperature. After addition, the mixture was stirred overnight, the precipitated solid was separated by filtration, washed with ether (200 mL) and dried in vacuo over KOH. Recrystallization from methanol-ether afforded 14.2 g (80%) of 20 as colorless crystals: mp 155° C. (dec); $^1$H NMR (CD$_3$OD) δ 2.96 (s, 3, NCH$_3$), 3.05 [t, 2, CH$_2$CH$_2$(NH)], 3.49–3.64 (m, 4, CH$_2$N—CH$_2$) and 3.8 (t, 2, $\overline{\text{CH}_2\text{CH}_2}$Br).

Anal. (C$_6$H$_{16}$Br$_3$N$_3$) C, 19.54; H, 4.39; Br, 64.69; N, 11.34.

S-2-[2′-(N-Methylamidino)ethylamino]ethylphosphorothioic Acid (21). To a stirred solution of Li$_3$SPO$_3$.4.7H$_2$O (7.7 g, 0.036 mol) in water (167 mL), compound 20 (13.9 g, 0.038 mol) was added. After dissolution, DMF (83.5 mL) was added, and the stirring was continued for 2 h. After refrigeration overnight, the product was filtered, washed first with DMF (300 mL) and then ether (1.6 L). The solid was dissolved in water (120 mL) and treated with acetonitrile until crystals separated. After cooling in an ice bath for 5 h, the colorless crystals were separated by filtration, washed with acetonitrile (330 mL), ether (330 mL) and dried in vacuo overnight to give 7 g (67%) of 21; mp 111°–113° C.; $^1$H NMR (D$_2$O) δ 2.95–3.05 [m, 7, —CH$_2$CH$_2$—C(N=)—NCH$_3$], 3.39–3.46 (m, 4, —S—CH—2—CH$_2$—NH) ; $^{31}$P NMR (D$_2$O) δ 15.57 (J=13 Hz). Anal. $\overline{\text{(C}_6\text{H}_{16}\text{N}_3\text{O}_3\text{PS.3H}_2\text{O)}}$ C, 24.55; H, 7.45; N, 14.16; P, 10.88; S, 11.09.

EXAMPLE 7

Synthesis of S-2-[2′-(4.5-Dihydroimidazoyl) Ethylaminolethyl Lithium Hydrogen Phosphorothioate (25)

N-[2-(Methoxyimino)ethyl]oxazolidinone (22). A stirred solution of 18 (100 g, 0.68 mol) in a mixture of dry CH$_2$Cl$_2$ (200 mL) and dry methanol (46 mL, 1.14 mol) was saturated with dry HCl at −10° C. to 5° C. and was stirred at 0° C. to 2° C. for 6 h. The mixture was poured into an ice cold solution of K$_2$CO$_3$ (300 g in 1 L of H$_2$O) along with stirring and cooling. After stirring for 10 min, the mixture was extracted with chloroform. The dried (Na$_2$SO$_4$) chloroform extract was evaporated. The residue was dried under high vacuum overnight to give 100 g (82%) of 22 as a pale yellow oil. This product was sufficiently pure to use in the next step. An analytical sample was prepared by column chromatography (SiO$_2$, 5% CH$_3$OH—CH$_2$Cl$_2$): $^1$H NMR (DMSO-$d_6$) δ 2.44 [t, 2, CH$_2$—C(NH)—], 3.36 [t, 2, —CH$_2$—CH$_2$—C(NH)—], 3.58 (m, 5, OCH$_3$, N—CH$_2$—CH$_2$—O), 4.23 (br m, 2, O—CH$_2$), 8.1 (s, 1, NH). Anal. (C$_7$H$_{12}$N$_2$O$_3$) : C, 48,62; H, 7.03; N, 16.27.

N-[2-(4,5-Dihydroimidazolyl)ethyl]oxazolidinone (23). A mixture of 25.8 g (0.15 mol) of N-[2-(methoxyimino)ethyl]oxazolidinone 22 and 9 g (0.15 mol) of ethylenediamine in 50 mL of absolute ethanol was refluxed for 30 min. After cooling to room temperature, the mixture was treated with ether until crystals separated and then was refrigerated for 3 days. The colorless crystals were filtered and dried to give 19.9 g (73%) of 23: mp 118°–123° C.; $^1$H NMR (CDCl$_3$) δ 2.54 (t, 2, —CH$_2$—C(=N) 3.57 (s, 4, =NCH$_2$CH$_2$—NH), 3.62 (m, 4, —CH$_2$NCH$_2$), 4.32 (m, 2, —OCH$_2$), 4.57 (b, NH). Anal. C$_8$H$_{13}$N$_3$O$_2$): C, 52.25; H, 7.15; N, 22.80.

2-[N-(4,5-Dihydroimidazoyl)ethylamino]ethyl Bromide Dihydrobromide (24). Compound 24 was prepared from 23 according to the procedure for preparing 10. Recrystallization from methanol afforded 71% of 24 as colorless crystals; mp 169°–173° C.; $^1$H NMR(DMSO-$d_6$) δ 3.04 [t, 2, —CH$_2$—(CH$_2$—)C=N), 3.44(m,4,—CH$_2$—NH—CH$_2$), 3.79, (t, 2, BrCH$_2$—), 3.85 (S, 4, =N—CH$_2$—C2—NH). Anal. (C$_7$H$_{16}$Br$_3$N$_3$): C, 21.92; H, 4.26; $\overline{\text{Br}}$, 62.86; N, 10.92.

S-2-[2′-(4,5-Dihydroimidazoyl)ethylamino]ethyl Lithium Hydrogen Phosphorothioate (25). To a stirred solution of 16.8 g (0.044 mol) of 24 was added 8 g (0.039 mol) of Li$_3$SPO$_3$.4.1H$_2$O in 195 mL of water. The mixture was cooled in an ice bath, and DMF (97.5 mL) was added. The ice bath was removed, and stirring was continued for 30 min. Dicyclohexylamine (30 mL) was added, and the resulting mixture was stirred for another min. The mixture was filtered, and the filtrate was added dropwise over a period of 20 min to 1.17 L of well-stirred DMF. After 20 min of stirring, the precipitate was filtered, washed first with DMF (700 mL), ether (1.8 L) and dried in vacuo overnight to afford 9 g (73%) of 25 as a white powder: mp >150° C. (dec) ; $^1$H NMR (D$_2$O) δ 2.65–3.04 (m, 8H) , 3.83 (s, 4H, =N—CH$_2$—CH$_2$—NH); $^{31}$P NMR (D$_2$O) δ 16.23 (t, J=11 Hz). Anal. (C$_7$H$_{15}$LiN$_3$O$_3$PS.H$_2$O): C, 30.71; H, 6.05; Li, 2.83; N, 14.92; P, 11.30; S, 11.62.

EXAMPLE 8

S-2-(2′-Amidinoethylamino)ethylphosphorothioic Acid (26)

This compound was prepared according to the method of Example 6, except intermediate amidino oxazolidinone was prepared by treating compound imino ester obtained from 18 with NH$_4$Cl in MEOH. 26 was obtained as a colorless solid: mp 177° C. (dec); $^1$H NMR (D$_2$O) δ 2.95–3.05 [m, 4,—CH$_2$—CH$_2$—C(N=)-], 3.4–3.49 (m, 4, —S—CH$_2$—CH$_2$—NH); $^{31}$P NMR (D$_2$O) δ 16.11 (t, J=11 Hz). Anal. (C$_5$H$_{14}$N$_3$O$_3$PS.0.5-H$_2$O): C, 25.48; H, 6.02; N, 17.32; P, 13.30; S, 13.92.

EXAMPLE 9

S-2-[2′-N-(p-Methoxybenzenesulfonyl)amidinoethylamino]ethyl Lithium Hydrogen Phosphorothioate (29)

N-[2-(p-Methoxybenzenesulfonylamidino)ethyl]oxazolidinone (27). A mixture of 10 g (0.058 mol) of imino ester derived from 18, 10.9 g (0.058 mol) of p-methoxybenzenesulfonamide and 50 mL of absolute ethanol was stirred and refluxed for 4 h. on cooling, an oil separated which began to solidify. After refrigerating overnight, the mixture was separated by filtration, washed with ether and dried to yield 15.3 g (79%) of 27 as colorless crystals: mp 115°–118° C.; $^1$H NMR (DMSO-$d_6$) δ 2.46 (t, 2, —CH$_2$C(N=)), 3.36 (m, 4, —CH$_2$—N—CH$_2$), 3.82 (s, 3, OCH$_3$), 4.12 (t, 2, —OCH$_2$), 7.07 (d, 2, Ar), 7.78 (d, 2, Ar), 7.95 (br s, 1 NH), 8.68 (br s, 1, NH).

Anal. ($C_{13}H_{17}N_3O_5S$): C, 47.88; H, 5.30; N, 12.75; S, 59.70.

2-[N-D-(Methoxybenzenesulfonyl)amidinoethylamino]ethyl Bromide Hydrobromide (28). Compound 27 (11 g, 0.034 mol) was added to 56 mL of a well stirred solution of HBr in AcOH, and the stirring was continued for 6 h. The precipitated product was separated by filtration, washed with ether and dried in vacuo overnight. This solid was dissolved in boiling methanol, cooled to room temperature, and treated with ether whereupon crystals separated. Cooling in an ice-salt bath for 3 h afforded 9.4 g (56%) of 28 as colorless crystals: mp 151°–152° C.; $^1H$ NMR (DMSO-$d_6$) δ 2.72 (t, 2, —$CH_2C$—(N═)), 3.17 (br s, 2, —$CH_2$—$CHC(N═)$ 3.42 (br m, 2, $BrCH_2$—$CH_2$—), 3.70 (t, 2, $BrCH_2$—), 3.83 (s, 3, —$OCH_3$), 7.08 (d, 2, Ar), 7.82 (d, 2, Ar), 7.99 (s, NH), 8.83 (br s, NH).

Anal. ($C_{12}H_{19}Br_2N_3SO_3$): C, 32.38; H, 4.34; Br, 35.86; N, 9.38, S, 7.25.

S-2-[2'-N-(p-Methoxybenzenesulfonyl)amidinoethylamino]ethyl Lithium Hydrogen Phosphorothioate (29). To a stirred solution of 7.45 g (0.017 mol) of 28 in 118 mL of water was added 3.52 g (0.017 mol) of $Li_3SPO_3.4.2H_2O$ in 17 mL of water. After 3 h, a gummy material settled. Enough DMF (~80 mL) was added until the mixture became homogeneous. Stirring was continued for 4 h. The mixture was diluted with 1.7 L of acetonitrile and refrigerated overnight. The crystallized product was collected, washed with 400 mL of acetonitrile, 400 mL of ether and dried in vacuo overnight to give 5.3 g (69%) of 29: mp 105° C. (dec); $^1H$ NMR ($D_2O$) δ 2.77-2.97 (m, 4, —$CH_2$—$CH_2C(N═)$), 3.27-3.35 (m, 4, —$SCH$—$CH$—$NH$—), 7.16 (d, 2, Ar), 7.88 (d, 2, Ar); $^{31}P$ NMR ($D_2O$) δ 15.69 (t, J=13 Hz).

Anal. ($C_{12}H_{19}LiN_3O_6PS_2.3 H_2O$): C, 31.76; H, 5.28; N, 9.31; P, 7.21; S. 14.06.

EXAMPLE 10

S-2-[2'-N-(R-Chlorobenzenesulfonyl)amidinoethylamino]ethyl Lithium Hydrogen Phosphorothioate (32)

N-[2-(R-Chlorobenzenesulfonylamidino)ethyl]oxazolidinone 30. A mixture of 10 g (0.058 mol) of imino ester obtained from 18, obtained by neutralizing HCl salt with $Na_2CO_3$, 11.2 g (0.058 mol) of p-chlorobenzenesulfonamide and 50 mL of absolute ethanol was stirred and refluxed for 4 h, cooled to room temperature, filtered, treated with ether until turbid and left in the refrigerator overnight. The product which separated as an oil solidified on seeding. The colorless solid was collected and dried to give 14 g (73%) of 30: mp 107°–112° C., $^1H$ NMR (DMSO-$d_6$) δ 2.50 (t, 2, —$CH_2C$—(N═)—), 3.40 (m, 4, —$CH_2$—N—$CH_2$), 4.14 [t, 2, —O—$CH_2$], 7.64 (d, 2, Ar), 7.85 (d, 2, Ar), 8.08 (s, 1, NH), 8.83, (s, 1, —NH).

Anal. ($C_{12}H_{14}ClN_3O_4S$): C, 43.24; H, 4.27; Cl, 10.78; N, 12.60; S. 9.72.

2-[N-(p-Chlorobenzenesulfonyl)amidinoethylamino]ethyl Bromide Hydrobromide (31). Compound 30 (13 g, 0.039 mol) was dissolved and stirred overnight in 130 mL of a saturated solution of HBr in acetic acid. Work up and recrystallization from methanol afforded 10 g (57%) of 31 as colorless needles: mp 181°–182° C.; $^1H$ NMR (DMSO-$d_6$) δ 2.75 (t, 2, —$CH_2C(N$—)—), 3.19 (t, 2, —$CH_2CH_2C(N$═)—), 3.41 (t, 2, $BrCH_2CH_2$—), 3.70 (t, 2, —$CH_2Br$), 7.66 (d, 2, Ar), 7.88 (d, 2, Ar), 8.12 (br s, —NH), 8.86 (br s, —NH), 8.98 (br s, —NH).

Anal. ($C_{11}H_{16}Br_2ClN_3SO_2$): C, 29.43; H, 3.61. Total halogen calculated as Br, 53.23 and as Cl, 23.62; N, 9.31; S, 7.18.

S-2-[2'-N-(p-Chlorobenzenesulfonyl)amidinoethylamino]ethyl Lithium Hydrogen Phosphorothioate (32). To a stirred solution of 6.6 g (0.03 mol) of $Li_3SPO_3.4.2H_2O$ in 160 mL of water was added 14.2 g (0.03 mol) of 31 followed by 80 mL of DMF. The clear solution was stirred for 5 h. The mixture was filtered, diluted with 3.1 L of acetonitrile and kept in the refrigerator for 2 days. The colorless crystals of 32 were filtered, washed first with acetonitrile (620 mL), ether (620 mL) and dried in vacuo for 2 days to give 10.6 g (80%) of 32: mp 161° C. (dec) $^1H$ NMR ($D_2O$) δ 2.79-2.99 (m, 4, —$CH_2CH_2$—$C(N$═)), 3.28-3.35 (m, 4, —S—$CH_2CH_2NH$—), 7.7 (d, 2, Ar), 7.9 (d, 2, Ar); $^{31}P$ NMR ($D_2O$) δ 15.63 (t, J=13 Hz).

Anal. ($C_{11}H_{16}ClLiN_3O_5PS_2.2H_2O$): C, 29.54; H, 4.61; Cl, 7.98; N, 9.19; P, 7.02; S, 14.49.

EXAMPLE 11

S-2-[2'-N-(r-Methylbenzenesulfonyl)amidinoethylamino]ethyl Lithium Hydrogen Phosphorothioate (35)

N-[2-(p-Methylbenzenesulfonylamidino)ethyl]oxazolidinone (33). A mixture of 10 g (0.058 mol) of N-[2-(methoxyimino)ethyl]oxazolidinone and 10 g (0.058 mol) of p-methylbenzenesulfonamide in 50 mL of absolute ethanol was stirred and refluxed for 4 h. The mixture was cooled to room temperature and filtered. The filtrate was treated with ether to induce crystallization. Further cooling in an ice-salt bath for 2 h afforded 14 g (78%) of 33 as colorless needles: mp 129°–134° C.; $^1H$ NMR (DMSO-$d_6$) δ 2.37 (s, 3, —$CH_3$), 2.47 [t, 2, —$CH_2$—C(N═)], 3.38 (m, 4, —$CH_2$—N—$CH_2$) 4.11 (t, 2, —$OCH_2$), 7.34 (d, 2, Ar), 7.74 (d, 2, Ar), 7.98 (s, 1, NH), 8.71 (s, 1, NH).

Anal. ($C_{13}H_{17}N_3O_4S$): C, 49.82; H, 5.49; N, 13.32; S, 10.18.

2-[N-(R-methylbenzenesulfonyl)amidinoethylamino]ethyl Bromide Hydrobromide (34). A solution of 10 g (0.032 mol) of 33 in 50 mL of acetic acid saturated with HBr was stirred for 6 h. The product was filtered, washed with ether (1 L) and dried in vacuo over KOH. Recrystallization from methanolether gave 8 g (58%) of 34 as colorless crystals: mp 172-173° C.; $^1H$ NMR (DMSO-$d_6$) δ 2.38 (s, 3, —$CH_3$), 2.69 (t, 2, —$CH_2$—C(N═)], 3.17 (t, 2, —$CH_2$—$CH_2$—C(N═)]. 3.4 (t, 2, $BrCH_2CH_2$), 3.68 (t, 2, $BrCH_2$), 7.36 (d, 2, Ar), 7.77 (d, 2, Ar), 8.03 (s, NH), 8.76 (b, NH), 8.84 (b, NH).

Anal. ($C_{12}H_{19}Br_2N_3SO_2$): C, 33.48; H, 4.48; Br, 37.18; N, 9.73; S, 7.51.

S-2[2'-N-(R-Methylbenzenesulfonyl)amidinoethylamino]ethyl Lithium Hydrogen Phosphorothioate (35). A solution of 7.35 g (0.035 mol) of $Li_3SPO_3.4.2H_2O$ in 35 mL of water was added dropwise to a stirred solution of 15.05 g (0.035 mol) of 34 in 455 mL of water over a period of 30 min. After addition, the stirring was continued for 3.5 h. The mixture was filtered, diluted with acetonitrile (3.5 L) and refrigerated overnight. The crystals were filtered, washed with acetonitrile (400 mL), ether (400 mL), and dried in vacuo overnight to afford 12 g (81%) of 35: mp 157° C. (dec); $^1H$ NMR ($D_2O$) δ 2.44 (s, 3, —$CH_3$), 2.77-3.0 (m, 4, —$CH_2CH_2$—C(N═)], 3.26-3.35 (m, 4, —$SCH_2CH_2N$), 7.41 (d, 2, Ar) 7.83 (d, 2, Ar). $^{31}$P NMR (D$_2$O) δ 15.63 (t, J=13 Hz).

Anal. (C$_{12}$H$_{19}$LiN$_3$O$_5$PS$_2$.2H$_2$): C, 34.14; H, 5.45; N, 0.65; P, 7.37; S, 15.41.

EXAMPLE 12

S-2-[2'-N-Methylsulfonyl)amidinoethylamino]ethyl Lithium Hydrogen Phosphorothioate (38)

N-[2-(Methylsulfonylamidino)ethyl]oxazolidinone (36). A mixture of 25.8 g (0.15 mol) of N-[ 2(methoxyimino)ethyl]oxazolidinone and 14.25 g (0.15 mol) of methanesulfonamide in absolute ethanol (100 mL) was stirred and refluxed for 4 h. The mixture was refrigerated for a week. The crystals were filtered, washed with ethanol (100 ml), ether (100 mL), and dried. Recrystallization from a chloroform-methanol-hexane mixture afforded 23 g (66%) of 36 as colorless crystals: mp 119°-120° C.; $^1$H NMR (DMSO-d$_6$) δ 2.46 (t, 2, —CH$_2$C(N=)], 2.86 (s, 3, —CH$_3$), 3.42 (t, 2, —CH$_2$—CH—C (N=)], 3.56 (t, 2, —CH$_2$CH$_2$O) , 4.24 (t, 2, —O—CH$_2$), 7.77 (s, 1, NH), 8.56 (s, 1, NH).

Anal. (C$_7$H$_{13}$N$_3$O$_4$S): C, 35.76; H, 5.59; N, 17.82; S, 13.66.

2-[N-(Methylsulfonyl)amidinoethylamino]ethyl Bromide Hydrobromide (37). A mixture of 16 g (0.068 mol) of 36 in 160 mL of 30-32% solution of HBr in acetic acid was vigorously stirred overnight. The precipitate was filtered, washed with acetic acid (80 mL), ether (1.6 L), and derived in vacuo. Recrystallization from methanol-ether afforded 17 g (71%) of 37 as colorless crystals: mp 132°-134° C.; $^1$H NMR (DMSO-d$_6$) δ 2.24 (b, 2, —CH$_2$CH$_2$C(N=) 2.48 (b, 2, BrCH$_2$CH$_2$], 2.85 (t, 2, —CH$_2$—C(N=)], 2.94 (s, 3, —CH$_3$), 3.76 (t, 2, BrCH$_2$), 7.81 (b, NH), 8.72 (b, NH), 8.89 (b, NH).

Anal. (C$_6$H$_{15}$Br$_2$N$_3$O$_2$S): C, 20.48; H, 4.28; Br, 45.18; N, 11.80; S, 9.03.

S-2-[2'-(N-methylsulfonyl)amidinoethylamino]ethyl Lithium Hydrogen Phosphorothioate (39). To a stirred solution of 8.68 g (0.04 mol) of Li$_3$SPO$_3$.4.7H$_2$O in 80 mL of water was added 16.0 g (0.045 mol) of 37. After dissolution, DMF (40 mL) was added, and the stirring was continued for 1 h 20 min. Dicyclohexylamine (20 mL) was added, and the mixture was stirred for an additional 2 h. The mixture was filtered, and the filtrate was stirred with acetonitrile (400 mL) for 4 h and refrigerated overnight. The oil that separated was carefully decanted, methanol (50 mL) was added, and the mixture was stirred for 15 min. The resulting precipitate was filtered, washed with methanol (30 mL), ether (100 mL) and dried in vacuo overnight to give 7.1 g (57%) of 38 as a colorless solid: mp 152° C. (dec); $^1$H NMR (D$_2$O) δ 2.57 (t, 2, —CH$_2$C(N=)], 2.88 (m, 6, —SCH$_2$CH$_2$NCH$_2$—]3.11 (s, 3, —CH$_3$); $^{31}$P NMR (D$_2$O) δ 16.3.

Anal. (C$_6$H$_{15}$LiN$_3$O$_5$PS$_2$): C, 22.85; H, 4.66; N, 13.38; P, 10.09; S, 20.90.

EXAMPLE 13

S-2-[2'-(N-Cyclopropylmethylcarboxamido)ethylamino]ethyl Dilithium Hydrogen Phosphorothioate (42)

N-Cyclopropylmethyl-β-chloroethoxycarbamyl-β-alanine Amide (39). A solution of 9.75 g (0.05 mol) of 7 in 50 mL of CHCl$_3$ was heated to reflux with 10 mL of SOCl$_2$ for 1 h. The solvents were re-moved under reduced pressure. The residue was dissolved in 15 mL of toluene and again evaporated to dryness under reduced pressure. A solution of the acid chloride prepared in 25 mL of CHCl$_3$ was added to a stirred solution of 4 g (0.055 mol) of cyclopropylmethylamine and 5 g of pyridine in 50 mL of CHCl$_3$ at dry ice-acetone temperature over a period of 30 min. The temperature was allowed to reach room temperature with continued stirring overnight. The precipitate was removed by filtration and washed with CHCl$_3$. The combined CHCl$_3$ solution was washed with saturated NaCl solution and dried (Na$_2$SO$_4$). The residue on evaporation was recrystallized from CH$_2$Cl$_2$-hexane to give 8.2 g (66%) of 39: mp 105°-106° C.; $^1$H NMR (CDCl$_3$) δ [0.21 (m, 2), 0.52 (m, 2), 0.92 (m, 1) cyclopropyl), 2.43 (t, 2, CH$_2$O), 3.46 (t, 2, NCH$_2$) 3.67 (dd, 2, NCH$_2$—<), 3.67 (t, ClCH$_2$) and 4.29 (t, 2, OCH$_2$).

Anal. (C$_{10}$H$_{17}$ClN$_2$O$_3$): C, 48.18; H, 6.91; N, 11.22; Cl, 14.23.

This experiment was repeated on larger scales to give 60-68% yields.

N[2-(N'-Cyclopropylmethylcarboxamido)ethyl]oxazolidinone (40). To a suspension of hexane washed NaH [(50% suspension), 1.5 g, 0.030 mol] in 40 mL of dry DMF was added a solution of 7.46 g (0.03 mol) of 39 in 25 mL of dry DMF over a period of 40 min. After stirring overnight, the precipitated NaCl was removed by filtration, and the solvents were removed under reduced pressure. The product was purified by silica gel column chromatography (300 g) using 10% MeOH/CH$_2$Cl$_2$ as the eluent. The pure fractions were combined and evaporated to a waxy solid. Recrystallization from a solvent system containing MeOH, ether and pet-ether gave 4.4 g (70%) of 40: mp 86°-87° C.; $^1$H NMR (CDCl$_3$) δ [0.22 (m, 2), 0.52 (m, 2), 0.95 (m, 1), cyclopropyl], 2.51 (t, 2, CH$_2$CO), 3.13 (dd, 2, NHCH$_2$—CH), 3.57 (t, 2, NCH$_2$), 3.66 [d, 2, CH$_2$—N-(O)—] and 4.39 (dd, 2, —CH$_2$O—).

Anal. (C$_{10}$H$_{16}$N$_2$O$_3$): C, 56.65; H, 7.61; N, 13.17.

This experiment was repeated on larger scales giving 65-70% yield.

2-(N-Cyclopropylmethylcarboxamidoethylamino)ethyl Bromide Hydrobromide (41). A solution of 14.85 g (0.07 mol) of 40 in 70 mL of 30% HBr in acetic acid was stirred overnight at room temperature. The white crystalline product obtained was collected by filtration and washed with precooled acetic acid (25 mL) and ether (300 mL) and was dried under vacuum. Recrystallization from MeOH-ether gave 16.1 g (70%) of 41: mp 116°-118° C.; $^1$H NMR (MeOH/CDCl$_3$) δ [0.21 (m, 2), 0.54 (m, 2), 0.97 (m, 1), cyclopropyl] 2.85 (t, 2, CH$_2$CO), 3.09 (dd, 2, NCH$_2$—<), 3.35 (dd, t, NCH$_2$CH$_2$O), 3.50 (t, 2, CH$_2$NCH$_2$) and 3.76 (t, 2, CH$_2$Br).

Anal. (C$_9$H$_{18}$Br$_2$N$_3$O): C, 32.78; H, 5.32; N, 8.40; Br, 48.53.

S-2-[2'-(N-Cyclopropylcarboxamido)ethylamino]ethyl Dilithium Phosphorothioate (42). To a solution of 11.04 g (0.03 mol) of 41 in 30 mL of distilled water and 15 mL of freshly distilled DMF was added 5.78 g (0.028 mol) of Li$_3$SPO$_3$.4.2H$_2$O in small portions. The resulting mixture was stirred for 3.5 h at room temperature. Dicyclohexylamine (13.4 g. 0.775 mol) was added to the mixture, and stirring was continued overnight. The precipitate formed was filtered, and the filtrate was diluted slowly while stirring with CH$_3$CN (300 mL) an ether (300 mL). The powdery solid material obtained after cooling to 16° C. was filtered and was washed with a mixture of CH$_3$CN (200 mL) and ether (200 mL) and dried under vacuum to give 5.65 g (26%) of 42: mp >260° C. (dec); $^1$H NMR (D$_2$O) δ [0.21 (m, 2), 0.53 (m, 2), 0.98 (m, 1), cyclopropyl], 2.47 (t, 2, $CH_2CO$) and 3.05 (d, $NHCH_2$—<) $^{31}P$ NMR ($D_2O$) 16.17 ppm (t, J=10 Hz).

Anal. ($C_9H_{17}Li_2N_2O_4SP.0.5H_2O$) C, 35.73; H, 5.76; Li, 4.51; N, 9.30; S, 10.79; P, 10.46.

EXAMPLE 14

S-2-[2'-(N-Carbamyl)carbamidoethylamino]ethyl Hydrogen Phosphorothioic Acid (46)

N-[2-(Cyanoamidino)ethyl]oxazolidinone (43). A mixture of N-[2-(methoxyimino)ethyl]oxazolidinone (31 g, 0.18 mol) and cyanamide (7.6 g, 0.18 mol) in dry methanol (150 mL) was stirred for 30–40 min. The precipitated solid 43 (14.1 g) was filtered, washed with methanol and dried. An additional 7.1 g (total yield 65%) of 4-3 was obtained on concentration and cooling of the mother liquor. The analytical sample prepared by recrystallization from methanol as colorless needles had a mp of 137°–139° C.: $^1H$ NMR (DMSO-$d_6$) δ 2.47–2.64 [b, 2, —$CH_2$—C(N=)—], 3.18–3.56 (b, 4, $CH_2$—N—$CH_2$), 4.24 (t, 2, —$OCH_2$), 8.34–8.8 (b, NH).

Anal. ($C_7H_{10}N_4O_2$): C, 46.31; H, 5.57; N, 30.70.

N-[2-(Carbamylamidino)ethyl]oxazolidinone Hydrobromide (44). A mixture of 43 (14 g, 0.08 mol) in 140 mL of 30–32% of HBr in acetic acid was vigorously stirred for I h. The precipitate was filtered, washed with acetic acid (100 mL) and ether (500 mL). The crystalline solid was treated with boiling methanol (50 mL), filtered, washed with methanol (70 mL), ether (200 mL) and dried in vacuo overnight to give 20.1 g (93%) of 44 as colorless crystals. The analytical sample prepared by recrystallization from methanol had a mp of 186°–188° C. (dec): $^1H$ NMR (DMSO-$d_6$) δ 2.72 [t, 2, —$CH_2$—C(N=)—], 3.6 (m, 4, $CH_2$—N—$CH_2$), 4.8 t, 2, —$OCH_2$).

Anal. ($C_4H_{13}BrN_4O_3$): 30.20; H, 4.77; N, 19.57.

2-[(Carbamylamidino)ethylamino]ethyl Bromide Dihydrobromide (45). A mixture of 44 (20 g, 0.07 mol) in 200 mL of 30–32% HBr in acetic acid was vigorously stirred along with gradual heating (temperature up to 120° C.) over a period of 1 h. The mixture was cooled and filtered. The colorless crystals were washed with acetic acid (200 mL), ether (200 mL) and dried in vacuo overnight to give 22.6 g (80%) of 45: mp 170°–172° C. (dec) (note: Incomplete reaction will occur if the stirring is not efficient); $^1H$ NMR (DMSO-$d_6$) δ 3.05 [t, 2, —$CH_2$—C(N=)], 3.5 (b, 4, —$CH_2$—NH—$CH_2$), 3.78, (t, 2, $BrCH_2$—).

Anal. ($C_6H_{15}Br_3N_4O$): C, 18.14; H, 3.80; Br, 59.98; N, 14.00.

S-2-[2'-(N-Carbamyl)carbamidoethylamino)ethyl Hydrogen Phosphorothioic Acid (46). To a stirred solution of $Li_3SPO_3.3.4H_2O$ (6.75 g. 0.035 mol) in $H_2O$ (175 mL), 45 (14 g, 0.035 mol) was added. After dissolution, the mixture was cooled in an ice bath, and DMF (87.6 mL) was added. The cooling bath was removed, and the mixture was stirred at room temperature for 2.5 h. The resulting reaction mixture was added dropwise over a period of 20 min to stirred DMF (1.4 L) and then stirred for 1 h. The solid was separated by filtration, washed with DMF (350 mL), ether (350 mL) and air dried. The crude product was dissolved in water (75 mL) and treated with acetonitrile (60 mL) when turbidity developed. On adding DMF to the mixture, the initial turbidity disappeared. Additional acetonitile was added until turbidity persisted and then refrigerated for 2 days. The amorphous solid was filtered, washed with DMF (350 mL), ether (1 L) and dried in vacuo to give 6.4 g (63%) of 46: mp 188°–198° C. (dec); $^1H$ NMR ($D_2O$) δ 3.0 (m, 4H) $^{31}P$ NMR ($D_2O$) δ 15.69 (t, J=13 Hz).

Anal. ($C_6H_{14}N_3O_5PS.H_2O$) C, 24.34; H, 5.30; N, 14.50; P, 10.55; S, 11.09.

S-2-[2'-($Δ^2$-1,2,4-Thiadiazolyl-1,1-dioxide)ethylamino]ethyl Lithium Hydrogen Phosphorothioate Acid (50)

N-[2-(Iodomethylsulfonylamidino)ethyl]oxazolidinone (47). To a vigorously stirred solution of N-[2-(methoxyimino)ethyl]oxazolidinone (25.8 g, 0.15 mol), in dry MeOH (100 mL) iodomethylsulfonamide (21.9 g, 0.1 mol) was added and stirred overnight. The precipitate was collected, washed with methanol (200 mL), ether (100 mL) and dried in vacuo to give 29 g (50%) of 47 as colorless crystals. An analytical sample was prepared by recrystallizing from $CH_3OH$: mp 118°–119° C.; $^1H$ NMR (DMSO-$d_6$) δ 2.50 [m, 2, —$CH_2$—C(N=)], 3.43 [t, 2, —$CH_2CH_2C(N=)$], 3.56 (m, 2, —O—$CH_2$—$CH_2$), 4.24 (m, 2, —$OCH_2$), 4.56 (s, 2, —$CH_2I$), 7.97 (b, NH), 8.79 (b, NH).

Anal. ($C_7H_{12}IN_3O_4S$) C, 23.31, H, 3.39; I, 35.06; N, 11.60; S, 8.89.

N-[2-($Δ^2$-1,2,4-Thiadiazoyl-1,1-dioxide)ethyl]oxazolidinone (48). To an ice bath cooled stirred suspension of hexane washed sodium hydride (3.2 g, 0.08 mol, 60% dispersion in mineral oil) in dry DMF (100 mL), a solution of 47 (10.8 g, 0.03 mol) in dry DMF (100 mL) was added dropwise over a period of 12 min. Temperature was maintained 5°–100° C. during addition. After addition, the cooling bath was removed and stirred for 15 min. Acetic acid (10 mL) was added dropwise to the mixture, followed by water (10 mL). (NOTE: Frothing will occur during quenching the reaction with acetic acid.) After stirring for 30 min, the mixture was evaporated in vacuo. The residue was dissolved in methanol (100 mL) and refrigerated for 2 days. The colorless crystals of 48 were collected, washed with methanol and were dried to give 5.9 g (85%) of product. An analytical sample was prepared by recrystallizing from $H_2O$: mp 126°–127° C.; $^1H$ NMR (DMSO-$d_6$) δ 2.64 [t, 2, —$CH_2$—C(N=)], 3.53 (m, 4, $CH_2$—N—$CH_2$), 4.26 (t, 2, —$OCH_2$), 4.39 (s, 2, —$CH_2$—$SO_2$).

Anal. ($C_7H_{11}N_3O_4S$): C, 36.09; H, 4.77; N, 17.98; S, 13.70.

2-[$Δ^2$-1,2,4-Thiadiazolyl-1,1-dioxide)ethylamino]ethyl Bromide Hydrobromide (49). A solution of 48 (8 g, 0.034 mol) in 80 mL of 30–32% HBr in acetic acid was vigorously stirred for 6.5 h. The precipitate was collected, washed with acetic acid (200 mL) and ether (500 mL). The solid was stirred in methanol (30 mL) for 15 min, filtered, washed with methanol (10 mL), ether (50 mL) and dried in vacuo overnight to get 8.8 g (74%) of 49 as colorless crystals: mp 141°–142° C.; $^1H$ NMR ($D_2O$) δ 3.02 [t, 2, —$CH_2$—C(N=)], 3.52 [t, 2, —$CH_2$—$CH_2$—C(N=)], 3.61 (m, 2, $BrCH_2CH_2$), 3.74 (m, 2, $BrCH_2$—), 4.60 (s, 2, —$CH_2SO_2$).

Anal. ($C_6H_{13}Br_2N_3SO_2$): C, 20.57; H, 3.74; Br, 45.47; N, 11.94; S, 9.06.

S-2-[2'-($Δ^2$-1,2,4-Thiadiazolyl-1,1-dioxide)ethylamino]ethyl Lithium Hydrogen Phosphorothioic Acid (50). To a stirred solution of $Li_3SPO_3.3.4H_2O$ (5.8 g, 0.03 mol) in water (150 mL), 49 (10.6 g, 0.03 mol) was added. After dissolution, the mixture was cooled in an ice bath, and DMF (75 mL) was added. The ice bath was removed, and the mixture was stirred at room temperature for 2.5 h. The mixture was added dropwise over a period of 10 min to stirred absolute ethanol (1.5 L) and then stirred for 1 h. The precipitate was collected and washed with ethanol (300 mL). It was dissolved in $H_2O$ (150 mL), added dropwise to stirred absolute ethanol (1.5 L) and then stirred for 1 h. The product was filtered, washed with ethanol (600 mL), ether (1.5 L) and dried in vacuo for 48 h to get 7.25 g (78%) of 50 as colorless powder: mp >170° C. (dec); $^1$H NMR ($D_2O$) δ 3.00 (m, 4H), 3.42 (m, 4H) , 4.61, (s, 2, —$CH_2$—$SO_2$); $^{31}$P NMR ($D_2O$) δ 15.69 (t, J=13 Hz).

Anal. ($C_6H_{13}LiHN_3O_5PS_2$): C, 23.43; H, 4.40; N, 13.36; P, 10.18; S, 20.19.

EXAMPLE 15

[N-(1-Methylpropyl)carboxamidoethyl]-2-thioxo-3-thiazolidine (54)

N-(1-Methylproply)-β-chloroethoxycarbamyl-β-alanine Amide (51). A solution of N-(1-methylpropyl)-β-chloroethoxycarbamyl-β-alaninyl chloride [prepared from 9.8 g (0.05 mol) of 7 and 10 mL of $SOCl_2$ as described earlier]in 20 ML of $CHCl_3$ was added to a solution of 4 g (0.055 mol) of sec-butylamine and 4.4 g (0.055 mol) of pyridine in 50 mL of $CHCl_3$ at dry ice-acetone temperature. After 16 h the reaction mixture was worked up as described earlier to give 7.05 g (58%) of 51: mp 97°-98° C.; $^1$H NMR ($CDCl_3$) δ 0.89 (t, 3, $CH_2CH_3$), 1.12 (d, 3, $CHCH_3$), 1.45 (m, 2, $CH_2$ $CH_3$) 2.40 (t, 2, $CH_2CO$) , 3.46 (m, 2, $NCH_2$) , 3.65 (t, 2, $CH_2Cl$), 3.92 (m, 1, $NHCH$—) and 4.29 (t, 2, —$CH_2OCO$).

Anal. ($C_{10}H_{19}ClN_2O_3$): C, 47.97; H, 7.65; N, 11.13; Cl, 14.08.

This experiment was repeated on a 0.8 mol scale to give a 67% yield.

N-[2-N'-(-Methylpropyl)carboxamido)ethyl]oxazolidinone (52).

The experiment was conducted as described for the preparation of 9. Thus, 15.0 g (0.06 mol) of 51 was cyclized with 3.0 g (0.06 mol) of hexane washed NaH. The crude product was obtained as a thick syrup after workup. Chromatography on silica gel (800 g) using 10% $MeOH/CH_2Cl_2$ as eluent gave 8.98 g (70%) of 52 as a viscous oil. The analytical sample was obtained as a waxy solid: $^1$H NMR ($CDCl_3$) δ 0.89 (t, 3, $CH_2CH_3$), 1.11 (d, 3, $CHCH_3$), 1.46 (m, 2, $CH_2CH_3$), 2.49 (t, 2, $CH_2CO$), 3.55 (t, 2, $NCH_2CH_2CO$), 3.67 (dd, 2, $OCH_2CH_2$ N), 3.86 (m, 1, N—$CH$—), 4.32 (dd, 2, $OCH_2$—$CH_2N$) and 7.24 (d, 1, NH).

Anal. ($C_{10}H_{18}N_2O_3$·0.5$CH_3OH$) C, 54.40; H, 8.61; N, 12.17.

2'-[N-(1-Methylpropyl)carboxamidoethylamino]ethyl Bromide Hydrobromide (53). The bromide hydrobromide (53) was obtained by ring opening the oxazolidinone with HBr/AcOH as described for 10. Thus, 3.63 g (0.017 mol) of 52 was stirred overnight with 15 mL of 30% HBr/AcOH. The crystalline material obtained was recrystallized from MeOH/ether to give 4.06 g (64%) of 53: mp 122°-127° C.; NMR ($D_2O$) δ 0.85 (t, 3, $CH_2CH_3$), 1.11 (d, 3, —$CHCH_3$), 1.45 (m, 2, —$CH_2CH_3$) 2.73 (t, 2, $CH_2CO$) , 3.39 (t, 3, $NHCH_2CH_2CO$), 3.55 (t, $BrCH_2$—) and 3.72 (m, 3, NH$CH$— and $BrCH_2CH_2N$).

Anal. ($C_9H_{18}BrN_2O$·1.5HBr): C, 29.04; H, 5.58; N, 7.52; Br, 53.51.

[N-(1-Methylpropyl)carboxamidoethyl]2-thioxo-3-thiazolidine (54). To a stirred solution of $Na_2CS_3$ (prepared by stirring 4.96 g (0.02 mol) of $Na_2S·9H_2O$ and 1.52 g (0.02 mol) of $CS_2$ along with ~ 0.5 g (aliquat 336 for 90 min) was added 53 (7.5 g, 20 mmol) and LiOH.-$H_2O$ (42 g, 10 mmol). Immediately, the deep red color of $Na_2CS_3$ was discharged, and the mixture was further stirred for 30 min. The mixture was extracted with $CH_2Cl_2$ (2×100 mL) , and the organic fraction was washed with NaCl solution and was dried over $Na_2SO_4$. The residue on evaporation was applied to a silica gel column (300 g) and was eluted with 5% MeOH in $CH_2Cl_2$. The pure fraction was collected and crystallized from $CH_2Cl_2$/pet. ether to give 2.33 g (47%) of 54: mp 117°-119° C.; MS calcd.: M+ ion 246.0861; found: M+ 246.0856. $^1$H NMR ($CDCl_3$) δ 0.96 (t, 3, $CH_2CH_3$), 1.16 (d, 3, $CHCH_3$), 1.47 (m, 2, $CH_2CH_3$), 2.78 (t, 2, $CH_2CO$), 3.48 (t, 2, S—$CH_2$), 3.87 (m, 1, $NHCH(CH_3)$), 4.08 (t, 2, $NCH_2CH_2CO$), 4.17 (t, 2, $SCH_2CH_2N$).

Anal. ($C_{10}H_{18}N_2OS_2$): C, 49.01; H, 7.57; N, 11.43; S, 26.21.

EXAMPLE 16

4-(3-tert-Butylomycarbamidopropyl)-5,6-dihydro-1,2,4-3(4H)dithiazinethione (55)

To a solution of WR2721 (1) (25.68 g, 0.12 mol) and triethylamine (36.36 g, 0.36 mol) in 100 mL $H_2O$ at room temperature was added a solution of di-tert-butyl-dicarbonate (26.16 g, 0.12 mol) in 100 mL of dioxane. After stirring overnight, carbon disulfide (10.03 g, 0.13 mol), followed by a 50% solution of NaOH (21.6 mL, ~ 0.27 mol) were added, and stirring continued for 3 h. A solution of iodine (~ 35 g, 0.137 mol) in $CH_2Cl_2$ was added, and the mixture was stirred for 45 min. The $I_2$ color was almost discharged and solid was precipitated. The mixture was filtered, and the residue was washed with $CH_2Cl_2$. The organic layer was separated, and the aqueous layer was extracted with $CH_2Cl_2$. The combined $CH_2Cl_2$ fraction was washed with a dilute sodium sulfite solution and $H_2O$ and was dried over $Na_2SO_4$. The residue obtained on evaporation was applied to silica gel (i kg) and was sequentially eluted with $CH_2Cl_2$(1 L) and 5% $MeOH/CH_2Cl_2$.

The second pure fraction from the column was evaporated to dryness and crystallized from $CH_2Cl_2$/hexane to give 6.84 g (18.5%) of 55: mp 104°-105° C.; $^1$H NMR ($CDCl_3$) δ 1.44 [s, 9, $C(CH_3)_3$]. 1.96 (m, 2, $NCH_2CH_2$—$CH_2N$) , 3.17 (m, 2, $CH_2NHC(O)$—], 3.4 (m, 2, S—$CH_2$—), 3.89 (m, 2, $NCH_2$—$CH_2S$), 4.11 (dd, 2, —C(S)N—$CH_2$).

Anal. ($C_{11}H_{20}N_2O_2S_3$): C, 42.75; H, 6.57; N, 9.06; S, 31.03. Compound 22

4-(3-Aminopropyl)-5,6-dihydro-1,2,4-3(4H)-dithiazinethione (56). A solution of 55 (6.05 g, 0.02 mol) in 50 mL of dry $CH_2Cl_2$ was stirred with 10 mL of trifluoroacetic acid at room temperature until TLC analysis indicated that all had reacted (~ 45 min). The reaction mixture was concentrated and the resulting product dried under vacuum. The residue was dissolved in 3% HCl in MEOH (400 mL) and evaporated to dryness. Recrystallization from MeOH/$Et_2O$ gave 3.46 g (73%) of 56 as needle-shaped crystals: mp 174°-176° C.; $^1$H NMR ($CD_3OD$) δ 2.17 (m, 2, $NHCH_2CH_2CH_2N$), 3.01 (t, 2, $CH_2S$—S), 3.5 (m, 1, (S)$NCH_2CH$), 3.96 (m, 2, $CH_2CH_2NH_2$), 4.21 t, s, N—$CH_2CH_2$—S—).

Anal. ($C_6H_{12}N_2S_3$·HCl): C, 29.49; H, 5.38; N, 11.40 S, 39.18; Cl, 11.52.

EXAMPLE 17

4-(2'N-Carbamidoethyl)-5,6-dihydro-1,2,4-3(4H)dithiazinethione (57). To a solution of S-2-(carboxamidoethylamino)ethyl lithium hydrogen phosphorothioate (12) [generated in situ from (carboxamidoethylamino)ethyl bromide hydrobromide] 17.94 g, 0.065 mol) and (LiO)$_3$PS (15.16 g, 0.072 mol) in 50 mL H$_2$O and 25 mL ETOH] was added carbon disulfide (6.0 g, 0.078 mol) and a 50% solution of NaOH (20 mL), and the mixture was stirred for 3.5 h. A saturated solution of I$_2$ in CH$_2$Cl$_2$ was added in portions until a faint color of I$_2$ remained. The mixture was filtered, and the residue was washed with CH$_2$Cl$_2$. The filtrate was extracted with CH$_2$Cl$_2$, and the combined organic fractions were washed with a dilute solution of Na$_2$SO$_3$, H$_2$O and was dried over Na$_2$SO$_4$. The residue on evaporation was chromatographed on silica gel (900 g) and eluted with 5% MeOH/CH$_2$Cl$_2$. The pure fraction was evaporated to dryness and recrystallized from CH$_2$Cl$_2$/hexane to give 2.25 g (16%) of 57: mp 131°-133° C.; $^1$H NMR (CDCl$_3$) δ 2.57 (t, 2, CH$_2$CO), 3.46 (t, 2, CH$_2$CH$_2$S—), 3.95 (t, 2, NCH$_2$CH$_2$S) and 4.14 (NCH$_2$CO).

Anal. (C$_6$H$_{10}$N$_2$OS$_3$): C, 32.47; H, 4.54; N, 12.58; S, 43.32.

EXAMPLE 18

N-(2'-Amidinoethyl)aminoethanethiol Dihydrochloride (58). A solution of S-2-(2'-amidinoethylamino)ethyl phosphorothioic acid 26 (example 8 in the application) (12.3 g, 0.052 mol) in concentrated HCl (50 mL) was stirred at room temperature for 58 h. After evaporating the mixture in vacuo at room temperature, the residue was dissolved in absolute ethanol (100 mL). To the stirred solution, ether (300 mL) was added and stirred for 1 h. The solid was filtered, washed with a mixture of absolute ethanol and ether (1:3, 400 mL) and dried in vacuo for 2 days to give 10.95 g (92%) of 58 as colorless hygroscopic crystals: mp 100°-105° C.; $^1$H NMR (D$_2$O) δ 2.88 (t, 2, —CH$_2$SH), 2.99 (m, 2, —CH$_2$—C(N=)], 3.34 (t, 2, —CH$_2$—CH$_2$—SH), 3.49 [m, 2, CH$_2$—CH$_2$—C(N=)].

Anal. (C$_5$H$_{15}$Cl$_2$N$_3$S.O.5H$_2$O): C, 26.18; H, 7.04; Cl, 31.00; N, 18.32; S, 13.90.

EXAMPLE 19

S-2-[(2'-Cyclopropylmethylamidino)ethylamino]ethyl Phosphorothioic Acid (61)

N-[2-Cyclopropylmethylamidino]ethyloxazolidinone Hydrochloride (59). A solution of N-(cyanoethyl)oxazolidinone 18 (30 g, 0.21 mol) in dry methanol (10.9 g, 0.34 mol) and dry CH$_2$Cl$_2$ (60 mL) was saturated with dry HCl at −15° to 0° C. The mixture was then stirred for 6 h at 0°-20° C. The mixture was evaporated and dried in vacuo for 1 h. The crystalline imidoester hydrochloride was dissolved in dry methanol (120 mL) and cooled to −15° C. To the stirred solution cyclopropylmethylamine (31.2 g, 0.44 mol) was added in drops over a period of 20 min while maintaining the temperature at −15 to 0° C. The mixture was then stirred at −10° C. for 45 min and evaporated. The residue was dissolved in methanol, treated with ether until turbid and was refrigerated for 6 days. The colorless crystalline material was collected and dried to give 59 (28.7 g, 55%), mp 86°-88° C. $^1$H NMR (DMSO—d$_6$) δ 0.28 (m, 2, —CH—CH$_2$), 0.55 (m, 2, —CH—CH$_2$), 1.05 (m, 1, —CH), 2.68 [t, 2, —CH$_2$—C(N=)], 3.07 (d, 2, —NH—CH$_2$), 3.54 [t, 2, —CH$_2$—CH$_2$—C(N=)], 3.67 (t, 2, —O—CH$_2$—CH$_2$). 4.30 (t, 2, —OCH$_2$).

Anal. (C$_{10}$H$_{18}$ClN$_3$O$_2$): C, 48.20; H, 7.39; Cl, 14.40; N, 16.87.

2-Cyclopropylmethylamidino)ethylamino]ethyl Bromide Dihydrobromide (60). A solution of 59 (24 g, 0.1 mol) in 240 mL of 30–32% HBr in acetic acid was stirred overnight. The precipitated crystals were filtered, washed with acetic acid (240 mL), ether (2 L) and dried in vacuo overnight to give 60 (18.2 g, 45%): mp 216°-222° C. (dec), $^1$H NMR (DMSO-d$_6$) δ 0.28 (m, 2, —CH—CH$_2$), 0.57 (m, 2, —CH—CH$_2$), 1.08 (m, 1, —CH), 2.86 [t, 2, —CH$_2$—C(N=)—], 3.07 (d, 2, NHCH$_2$), 3.34 [t, 2, —CH$_2$CH$_2$—C(N=)—], 3.48 (BrCH$_2$CH$_2$), 3.71 (BrCH$_2$—).

Anal. C$_9$H$_{20}$Br$_3$N$_3$: C, 26.46; H, 4.95; Br, 58.32; N, 10.23.

S-2-[(2'-Cyclopropylmethylamidino)ethylamino]-phosphorothioic Acid (61). To a stirred solution of Li$_3$SPO$_3$.3.4H$_2$O (10.8 g, 0. 056 mol) in H$_2$O (110 mL), 60 (25.98 g, 0.063 mol) was added, and the stirring was continued for 30 min. The mixture was added in drops over a period of 20 min to stirred DMF (2 L) and then stirred for 2.5 h. The solid was filtered, washed with DMF (200 mL) and ether (1 L). The crude product was dissolved in water (160 mL) and cooled to ∼3° C. (ice water bath). This solution was added to a stirred and cold (3° C.) suspension of ion exchange resin (water washed, 140 m (Biorad, H form, analytical grade) in water (170 mL) and then stirred at that temperature for 10 min. The resin was separated by filtration, washed with ice cold water (5×100 mL), and stirred with 3N NH$_4$OH (560 mL) for 15 min. The resin was filtered and washed with 3N NH$_4$OH (2×100 mL). The NH$_4$OH solution was evaporated and concentrated in vacuo to ∼ 40 mL on a rotatory evaporator at room temperature. This solution was added dropwise to stirred DMF (500 mL) followed by continued stirring for 1 h. The precipitate was filtered, washed with DMF (200 mL), ether (1.5 L) and dried in vacuo overnight. An $^1$H NMR spectrum of the product (10.8 g, 67%) thus obtained indicated impurities. Reprecipitation from H$_2$O-DMF did not improve the purity. When this material was treated with CH$_3$OH (75 mL), it appeared to go into solution. However, on sonication for 20 min, a fine precipitate formed. The precipitate was separated by filtration, washed with methanol (50 mL), ether (400 mL) and dried in vacuo for 48 h to give 4.0 g (21%) of 61 as colorless solid: mp 133°-135° C. $^1$H NMR (D$_2$O) δ 0.3 (m, 2, —CH—CH$_2$), 0.62 (m, 2, —CH—CH$_2$), 1.13 (m, 1, CH), 2.96 (m, 4), 3.15 (d, 2, —NHCH$_2$), 3.4 (m, 4). $^{31}$P NMR (D$_2$O) δ 15.63 (t, J=13 Hz).

Anal. (C$_9$H$_{20}$N$_3$O$_3$PS.H$_2$O): C, 35.94; H, 7.39; N, 13.78; P, 10.51; S, 10.51.

EXAMPLE 20

Radiation-Protective Evaluation

Results for the radiation-protective properties of 4a-c, 13a-b, 18a-b and 21 along with WR2721 and WR6458 for comparison are listed in Table 1. Test results were carried out at A. D. Little, Boston, MA, or the University of Louisville School of Medicine, Louisville, Ky., according to Klayman et al, (J. Med. Chem. 1969, 12, 510). Test results were provided by H. A. Musallam of the Walter Reed Army Institute of Research. Compounds were administered intraperitoneally by injection as a 2% by wt. solution 30 min prior to X-irradiation. The X-irradiation is measured in gigarads (GY) and the results show the percentage of mice surviving. A 30 day survival time was taken as the criterion for protection. The compositions of the present invention were compared with WR2721 and WR6458 for their effectiveness at providing radiation protection.

TABLE 1

RADIATION-PROTECTIVE PROPERTIES IN MICE[a]

| Compound | Structure | Approximate $LD_{50}$ (mg/kg) | Drug Dose (mg/kg) | Vehicle of Administration | Radiation Dose (GY) | 30-Day Survival % |
|---|---|---|---|---|---|---|
| 12 | $H_2NCCH_2CH_2NHCH_2CH_2SPO_3HLi$ (C=O) | >600[b] | 600<br>300 | 80% $H_2O$<br>20% $C_2H_5OH$ | 10 | 70<br>10<br>0 |
| 11 | $CH_3NHCCH_2CH_2NHCH_2CH_2SPO_3HLi$ (C=O) | >600 | 600<br>300 | $H_2O$ | 10 | 80<br>20 |
| 13 | $(CH_3)_3CNHCCH_2CH_2NHCH_2CH_2SPO_3Li_2$ (C=O) | >300 | 300<br>150<br>75 | $H_2O$ | 9.5 | 80<br>60<br>40 |
| 16 | $H_2NCCH_2CH_2NHCH_2CH_2SPO_3HLi$ (C=S) | >300 | 300<br>150<br>75 | $H_2O$ | 9.5 | 100<br>40<br>10 |
| 17 | $CH_3NHCCH_2CH_2NHCH_2CH_2SPO_3HLi$ (C=S) | >250 | 150<br>75<br>37.5 | 80% $H_2O$<br>20% $C_2H_5OH$ | 10 | 80<br>0<br>0 |
| 21 | $CH_3NHCCH_2CH_2NHCH_2CH_2SPO_3H_2$ (C=NH) | >150 | 150<br>75<br>37.5 | 85% $H_2O$<br>15% $C_2H_5OH^c$ | 9.5 | 80<br>50<br>30 |
| 26 | $H_2NHCCH_2CH_2NHCH_2CH_2SPO_3H_2$ (C=NH) | >150 | 150<br>75<br>37.5 | 85% $H_2O$<br>15% $C_2H_5OH^c$ | 9.5 | 100<br>70<br>10 |
| 25 | pyrrolidine-N-CH2CH2NHCH2CH2SPO3HLi | >100 | 100<br>75<br>37.5 | $H_2O$ | 9.5 | 80<br>20<br>0 |
| WR2721[b] | $H_2NCH_2CH_2CH_2NHCH_2CH_2SPO_3H_2$ | 1000 | 600<br>300<br>150<br>75 | | 10 | 100<br>100<br>40<br>40 |
| WR6458[d] | $H_2NCCH_2CH_2NHCH_2CH_2SPO_3H_2$ (C=O) | 130 | 50<br>25 | | 10 | 0<br>0 |

[a]Antiradiation tests in groups of ten mice against lethal γ radiation: 9.5 or 10 GY from $^{60}CO$ source 30 min after intraperitoneal dosing.
[b]No toxic deaths observed in 5 mice at this dose.
[c]Contains 0.3% of methyl cellulose.
[d]Taken from T. R. Sweeney, ibid.

The toxicity of 12 is in sharp contrast to the previously reported toxicity of WR6458. Whereas 12 prepared in this study showed no toxic deaths in five mice at doses of 600 mg/kg, WR6458 possessed an $LD_{50}$ of 130 mg/kg (T. R. Sweeney, ibid.). Moreover, 12 was 70% protective at 600 mg/kg.

Compound 16, the thioamide analog of 12, gave 100, 40 and 10% survival at 300, 150 and 75 mg/kg, whereas compound 26, the amidine analog of 12, led to 100, 70, 10% survival at 150, 75 and 37.5 mg/kg. The analogs 11, 13, 17, 21 and 25 all gave 80% protection at the highest dose tested.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A phosphorothioate compound of formula 5

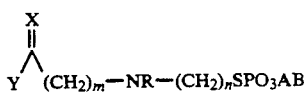

wherein
X equals S, N—R';
Y equals N—(R")R''', S—R";
R equals H, $C_{1-20}$ alkyl, benzyl, or phenyl;
R', R", and R''' is each independently H, $C_{1-6}$ alkyl, halosubstituted $C_{1-6}$ alkyl, $C_{3-6}$ cycloalkyl, $C_{3-6}$ cycloalkyl substituted $C_{1-6}$ alkyl, $H_2NC(O)$ or $SO_2R''''$;
wherein R'''' is phenyl, p-anisyl, p-chlorophenyl, tolyl, $C_{1-6}$ alkyl or amino;
m and n are each independently an integer from 1–4;

A and B are each independently H, $C_{1-6}$ alkyl or Li; or hydrates thereof.

2. The compound of claim 1, wherein X equals S, and Y equals N—(R") R'''.

3. The compound of claim 1 wherein X equals N-R' and Y equals N—(R")R'''.

4. S-2-(Thiocarbamidoethylanino)ethyl Lithium Hydrogen Phosphorothioate.

5. S-2-(2'-N-Methylthiocarbamidoethylamino)ethyl Lithium Hydrogen Phosphorothioate.

6. S-2-(2'-(N-Methylthioamidino)ethylamino) ethylphosphorothioic acid.

7. S-2-(2'-Amidinoethylamino)ethylphosphorothioic Acid.

8. A pharmaceutical composition comprising a radiation protective amount of a compound of formula 5

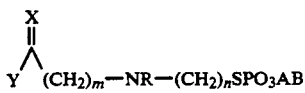

wherein
X equals S, N—R';
Y equals N—(R")R''', S—R";
R equals H, $C_{1-20}$ alkyl, benzyl, or phenyl;
R', R", and R''' is each independently H, $C_{1-6}$ alkyl, halosubstituted $C_{1-10}$ alkyl, $C_{3-6}$ cycloalkyl, $C_{3-6}$ cycloalkyl substituted $C_{1-6}$ alkyl, $H_2NC(O)$ or $SO_2R''''$;
wherein R'''' is phenyl, p-anisyl, p-chlorophenyl, tolyl, $C_{1-6}$ alkyl or amino;
m and n are each independently an integer from 1–4;
A and B are each independently H, $C_{1-6}$ alkyl or Li; or hydrates thereof; and
a pharmaceutically acceptable carrier.

9. The pharmaceutical composition of claim 8 wherein the compound of formula 5 is selected from the group consisting of:
S-2-(Thiocarbamidoethylamino)ethyl Lithium Hydrogen Phosphorothioate,
S-2-(2'-N-Methylthiocarbamidoethylamino)ethyl Lithium Hydrogen Phosphorothioate,
S-2-(2'-(N-Methylamidino)ethylamino)ethylphosphorothioic Acid,
S-2-(2'-Amidinoethylamino)ethylphosphorothioic Acid,
S-2-(2'-N-Methylcarbamidoethylamino)ethyl Lithium Hydrogen Phosphorothioate, and
S-2-(2'-(tert-Butylcarbamido)ethylamino)ethyl Dilithium Phosphorothioate or mixtures thereof.

10. A method of reducing the cytotoxic effects on healthy cells which are subjected to irradiation or chemotherapy comprising administering a radiation protective amount of a pharmaceutical composition according to claim 8.

11. The pharmaceutical composition of claim 8, wherein said compound of Formula 5 is selected from the group consisting of:
S-2-[2'-Methylcarbmidoethyl-amino]ethyl Lithium Hydrogen Phosphorothioate, S-2-[2(2'-Carbamidoethylamino)]ethyl Lithium Hydrogen Phosphorothioate, and S-2-[2'-(Tert-Butylcarbamido)ethylamino]ethyl Dilithium Phosphorothioate.

* * * * *